US008127769B2

(12) United States Patent
Walker

(10) Patent No.: US 8,127,769 B2
(45) Date of Patent: Mar. 6, 2012

(54) INTEGRATED ORAL APPLIANCE FOR SLEEP-DISORDERED BREATHING

(75) Inventor: Elijah Charles Walker, Silver Spring, MD (US)

(73) Assignee: Dreamscape Medical LLC, Atlanta, GA (US)

( * ) Notice: Subject to any disclaimer, the term of this patent is extended or adjusted under 35 U.S.C. 154(b) by 564 days.

(21) Appl. No.: 12/273,534

(22) Filed: Nov. 18, 2008

(65) Prior Publication Data

US 2009/0241969 A1 Oct. 1, 2009

Related U.S. Application Data

(60) Provisional application No. 60/988,794, filed on Nov. 18, 2007.

(51) Int. Cl.
*A61F 5/56* (2006.01)
*A61C 3/00* (2006.01)
*A61C 5/00* (2006.01)

(52) U.S. Cl. ............................. 128/848; 433/6; 433/140
(58) Field of Classification Search .................. 128/848; 602/902; 433/140, 6
See application file for complete search history.

(56) References Cited

U.S. PATENT DOCUMENTS

| | | | | |
|---|---|---|---|---|
| 3,536,069 A * | 10/1970 | Gores | ........................ | 128/861 |
| 4,676,240 A | 6/1987 | Gardy | | |
| 4,884,581 A * | 12/1989 | Rescigno | ...................... | 128/869 |
| 5,052,409 A | 10/1991 | Tepper | | |
| 6,467,484 B1 * | 10/2002 | De Voss | ........................ | 128/848 |
| 6,634,884 B2 * | 10/2003 | Phillips | ........................ | 433/138 |
| 6,729,335 B1 | 5/2004 | Halstrom | | |
| 6,766,802 B1 | 7/2004 | Keropian | | |
| 2008/0041396 A1 | 2/2008 | Lucker | | |
| 2008/0210244 A1 | 9/2008 | Keropian | | |
| 2010/0163043 A1 | 7/2010 | Hart et al. | | |

OTHER PUBLICATIONS

Hoekema, A., et al., "Obstructive Sleep Apnea Therapy," Journal of Dental Research, 2008, pp. 882-887, vol. 87, Issue 9, Sage Publications, USA.
Zozula, Rochelle, et al., "Compliance with continuous positive airway pressure therapy: assessing and improving treatment outcomes," Current Opinion in Pulmonary Medicine, Nov. 2001, pp. 391-398, vol. 7, Issue 6, Wolters Kluwer/Lippincott Williams & Wilkins, United Kingdom.
Hoffstein, Victor, "Review of oral appliances for treatment of sleep-disordered breathing," Sleep and Breathing, Mar. 2007, pp. 1-22, vol. 11, No. 1, Springer Berlin, Germany.
Chen, Hui, et al., "Three-dimensional computer-assisted study model analysis of long-term oral-appliance wear. Part 2. Side effects of oral appliances in obstructive sleep apnea patients," American Journal of Orthodontics & Dentofacial Orthopedics, Sep. 2008, pp. 408-417, vol. 134, Issue 3, Elsevier Inc., USA.
Vanderveken, Olivier M., et al., "Comparison of a Custom-made and a Thermoplastic Oral Appliance for the Treatment of Mild Sleep Apnea," American Journal of Respiratory and Critical Care Medicine, 2008, pp. 197-202, vol. 178, American Thoracic Society, New York, NY, USA.
Schoenhofer, B., et al., "Value of various intra- and extraoral therapeutic procedures for treatment of obstructive sleep apnea and snoring," Medizinische Klinik, Mar. 15, 1997, pp. 167-174, vol. 92, No. 3, Urban & Vogel, Germany.

* cited by examiner

*Primary Examiner* — Patricia Bianco
*Assistant Examiner* — Victoria J Hicks
(74) *Attorney, Agent, or Firm* — Hunton & Williams LLP

(57) ABSTRACT

An integrated oral appliance treats breathing obstruction and restriction in the upper airway during sleep with a cantilevered tongue restraint coupled through spring-force to a rigid bracket that is attached to a tray shaped to engage dentition.

27 Claims, 10 Drawing Sheets

INTEGRATED ORAL APPLIANCE FOR SLEEP-DISORDERED BREATHING

RELATED APPLICATIONS

The present application claims the benefit of priority of U.S. provisional patent application No. 60/988,794, filed Nov. 18, 2007, which is incorporated by reference herein.

FIELD OF THE INVENTION

The present invention application pertains to oral (i.e. intraoral) appliances for treating sleep-related breathing disorders. More particularly, this invention application pertains to an oral appliance to enhance breathing during sleep by preventing and alleviating upper airway obstruction and restriction resulting from sleep-related breathing disorders such as snoring, obstructive sleep apnea, obstructive sleep hypopnea, or upper airway resistance.

BACKGROUND OF THE INVENTION

Sleep is a fundamental need and appears to be required for human survival. However, for many people diagnosed with sleep apnea, going to sleep can be a dreaded experience due to the lack of restful sleep. Sleep apnea (apnea meaning a cessation of airflow) is a relatively common and potentially life-threatening sleep disorder that impacts millions of people in the United States and around the world.

Obstructive sleep apnea (OSA), obstructive sleep hypopnea, and upper airway resistance are characterized by upper airway abnormalities that result in airway collapse and complete or partial obstruction of airflow into the lungs. Upper airway (i.e. upper respiratory tract, or airway) abnormalities include: a smaller (than normal) airway cross-sectional area that subjects the pharynx to collapse; an enlarged tongue that can obstruct the airway by moving posteriorly (backward) into airway space during sleep; a retruding jaw that can increase tissue pressure surrounding the airway and subject it to collapse; an enlarged soft palate that can impinge on airway space when breathing; or compromised pharyngeal dilator muscles that fail to keep the airway open when inhaling, causing momentary obstruction of airflow. Fortunately, the brain usually detects this inability to breathe and briefly awakens the individual to reopen the airway. Unfortunately, these continuous disruptions in breathing have also been associated with increased blood pressure, stroke, and diabetes as well as other chronic disorders including death. Due to the variety of airway abnormalities that cause obstruction, and individual needs and preferences, no single solution has been found to be acceptable to all who suffer from OSA.

RELATED ART

Powered Apparatus Approaches

Various apparatus-based approaches (e.g. non-surgical and non-pharmacological) have been developed to treat snoring and/or sleep apnea which in general can be divided into two categories: 1. apparatus that require a power source and 2. apparatus that do not require a power source. Apparatus that require power sources (usually involving forced ventilation) include medical devices, such as Continuous Positive Airway Pressure (CPAP) devices, and negative pressure apparatus. Although CPAP devices have success rates of approximately 82.7% (Hoekema A, et al, "Obstructive Sleep Apnea Therapy", J Dent Res. 2008 September; 87(9):882-7), they suffer from low user compliance estimated to be approximately "25-50% with patients typically abandoning therapy during the first 2 to 4 weeks of treatment"; (Zozula, R. et al, "Compliance with continuous positive airway pressure therapy . . . ", Current Opinion in Pulmonary Medicine. 7(6):391-398, November 2001). Those who dislike CPAP give many reasons including: mask discomfort, difficulty adapting to the pressure, dislike being tethered to a machine, nasal irritation, sore throat, and allergies.

Non-Powered Apparatus Approaches: Oral Appliances

Non-powered apparatus (typically oral appliances) offer additional solutions for snoring or sleep apnea. Oral appliances can generally be separated into two types: Mandibular Repositioning Appliances, (e.g. U.S. Pat. No. 6,729,335, Halstrom, May 4, 2004) and Tongue Retainer appliances. Mandibular Repositioning Appliances (MRAs, sometimes known as mandibular advancement appliances) purport to reposition the mandible anteriorly to further open the airway to prevent its obstruction.

Tongue Retainer (TR) appliances are not used very often, and in general, they either use a medium such as a vacuum to hold/pull the tongue or they use a direct contact device to hold/restrain the tongue during sleep. Vacuum-type TRs may be recommended when users lack adequate teeth or when the lower jaw can't be advanced. One vacuum-type TR, (U.S. Pat. No. 4,676,240, Gardy, Jun. 30, 1987) purports to provide a way to hold the tongue forward in a chamber that generates a vacuum when the tongue begins to fall and also purports to allow oral breathing.

A direct contact type of TR (e.g. U.S. Pat. Application Pub. 2008/0041396 A1, Lucker, Feb. 21, 2008) purports to restrain the tongue using a rigid flat tab at the back of the tongue and uses another rigid tab-like component in the area of the soft palate. Another TR appliance (e.g. U.S. Pat. No. 6,766,802, Keropian, Jul. 27, 2004) purports to hold the tongue down using a rigid bar-like device.

Shortcomings of Prior Art

Prior art offers a variety of purported solutions along with significant drawbacks. Oral appliances (MRA, TR, etc.) in general have treatment success rates of approximately 54%, and compliance rates of 56-68%. (Hoffstein V, "Review of oral appliances for treatment of sleep-disordered breathing", Sleep Breath. 2007 March; 11(1):1-22). MRA users have experienced mixed success, with some patients experiencing potentially harmful dental changes and/or temporomandibular joint pain. A study reported that with long term use (88.4+/−26.7 months) there were significant dental changes including "mandibular arch width increased more than maxillary arch width" (Chen H, et al, "Three-dimensional . . . Part 2. Side effects of oral appliances . . . ", Am J Orthod Dentofacial Orthop. 2008 September; 134(3):408-17).

Pre-fabricated thermoplastic (boil and bite) MRAs have been determined to be ineffective and "cannot be recommended as a therapeutic option nor can it be used as a screening tool to find good candidates for mandibular advancement therapy" (Vanderveken, O M, et al, "Comparison of a custommade and a thermoplastic oral appliance for the treatment of mild sleep apnea.", Am J Respir Crit Care Med 2008; 178: 197-202).

Vacuum-type TR devices that purport to hold the tongue suffer from low compliance rates, reported to be 25% in one study (e.g. 75% non-compliance) and low efficacy i.e. low treatment success, (Schonhofer, B et al, "Value of various intra- and extraoral therapeutic procedures for obstructive sleep apnea and snoring", Med Klin (Munich, 1997 Mar. 15; 92 (3):167-74 9173209).

Part of the difficulty of restraining or holding the tongue is due to the typically wet, slippery nature of the tongue. Saliva is continuously produced in the oral cavity at a rate of approximately 1.5 liters per day, which increases when foreign objects are added. Additionally, glycoproteins in saliva (which provide its lubricative characteristic), increase the difficulty of holding the tongue.

Thus there remains a need for a treatment apparatus that does not require forced ventilation, or being tethered, and is effective in restraining intraoral tissue including the tongue and or mandible without adverse effects such as discomfort, pain, tissue dysfunction, or injury.

It would be advantageous to provide an effective oral appliance to maintain upper airway patency during sleep, thus preventing obstructions and snoring without adverse effects.

It would be advantageous to provide an oral appliance to maintain airway patency comprising mandible repositioning and tongue restraint to improve treatment effectiveness and comfort.

It would be advantageous to provide an oral appliance comprising a comfortable, easily adjustable mandible repositioning method.

It would be advantageous to provide an oral appliance comprising bristles to retain the tongue without excessive force.

It would be advantageous to provide an oral appliance comprising a built-in air conduit to provide breathable air via the oral cavity while keeping the mouth closed thus preventing and bypassing obstructions and nasal restrictions.

The aforementioned and other advantages, features and characteristics of the present invention, as well as the methods of operation and functions of the related elements of structure and the combination of parts and economies of manufacture, will be more apparent upon consideration of the following detailed description and claims, with reference to the accompanying drawings; all of which form a part of this specification, wherein like reference numerals designate corresponding elements in the various figures. It should also be understood that the drawings are for the purpose of illustration and description and are not intended to specify the limits of the invention. Nor is the size, scale or orientation of elements shown in the drawings intended to reflect actual size, scale or proportion. Additionally, the method of the present invention includes any description herein of how the apparatus functions or is used, irrespective of whether such description is specifically identified as method disclosure.

SUMMARY OF THE INVENTION

In accordance with the present invention, a unique oral appliance integrates several novel features to treat sleep-related breathing disorders associated with upper airway abnormalities. The appliance firmly grips the users' upper and lower dentition using custom fitted u-shaped trays (i.e. mouthpiece). An adjustable bracket attached to the trays facilitates movement of the lower tray to advance the mandible to prevent airway closure. The tongue-restraint-ac (TRAC) component, containing a hollow middle, is attached to the bracket in a cantilevered fashion to apply a compressive spring-loaded force to the dorsal surface of the tongue. Novel flexible bristles, built into the bottom of the TRAC, (proven to be effective in a reduction to practice) engage the tongue to prevent it from obstructing the airway. The hollow middle allows breathable air to flow (via the oral cavity) directly to the airway, bypassing nasal restrictions and/or airway obstructions.

BRIEF DESCRIPTION OF THE DRAWINGS

A complete understanding of the present invention may be obtained by reference to the accompanying drawings, when considered in conjunction with the subsequent, detailed description, in which.

For purposes of clarity and brevity, like elements and components will bear the same designations and numbering throughout the Figures.

DESCRIPTION OF THE PREFERRED EMBODIMENT

Figure 1:
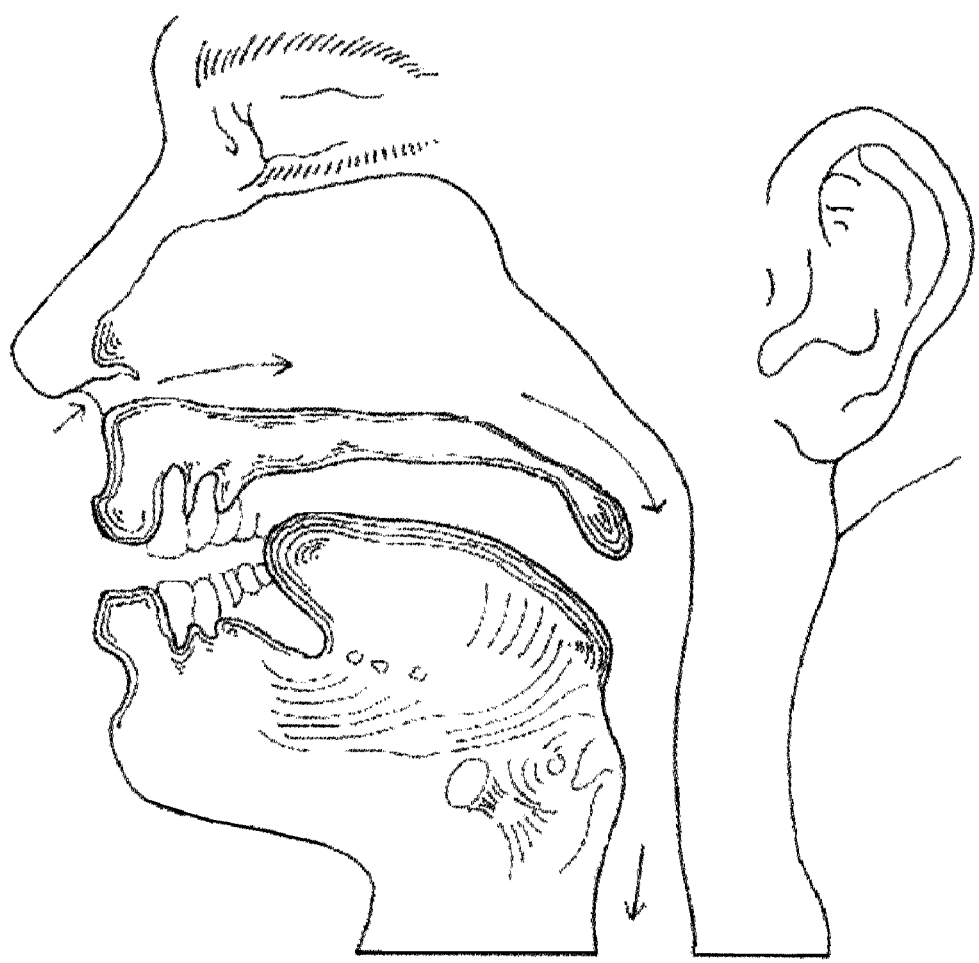
FIG. 1 is a left sectional view of an anatomical cross-section of a normal human upper airway including nasal cavity, oral cavity, and pharynx with arrows illustrating normal nasal airflow.

Accordingly, the preferred embodiment of the present invention comprises several unique features designed to overcome upper airway abnormalities experienced by those who suffer from sleep-related breathing disorders such as obstructive sleep apnea and snoring. Specifically, the integrated oral appliance 26 treats obstructive sleep apnea and snoring by preventing or mitigating airway closures by advancing the mandible to further open the airway and by retaining the tongue using flexible bristles 25. The present invention, as well as a preferred mode of use, objects and advantages, can be understood by referring to the following detailed description when read in conjunction with the accompanying drawings, wherein:

FIG. 1 is an anatomical cross-section of a normal human upper airway including nasal cavity, oral cavity, and pharynx with arrows illustrating nasal airflow.

Figure 2:
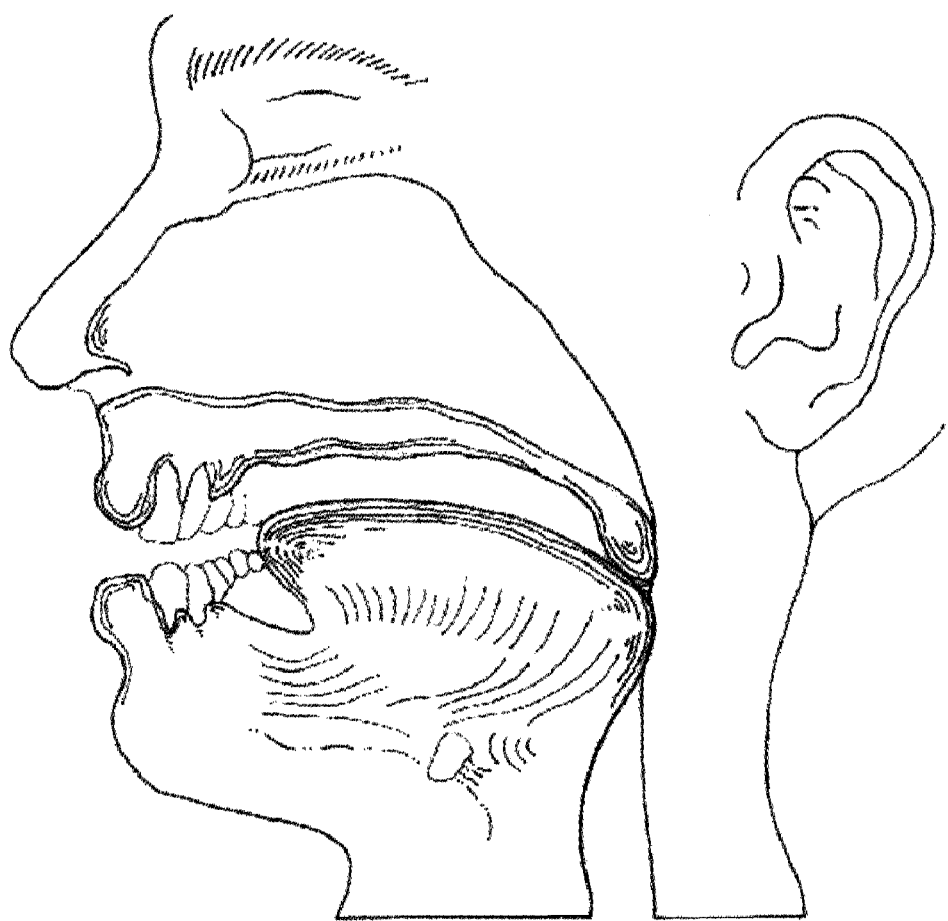
FIG. 2 is a left sectional view of an anatomical cross-section illustrating occlusion of the pharynx that can occur during obstructive sleep apnea.

FIG. 2 is a view similar to FIG. 1, illustrating occlusion of the pharynx that can occur during obstructive sleep apnea.

Figure 3:
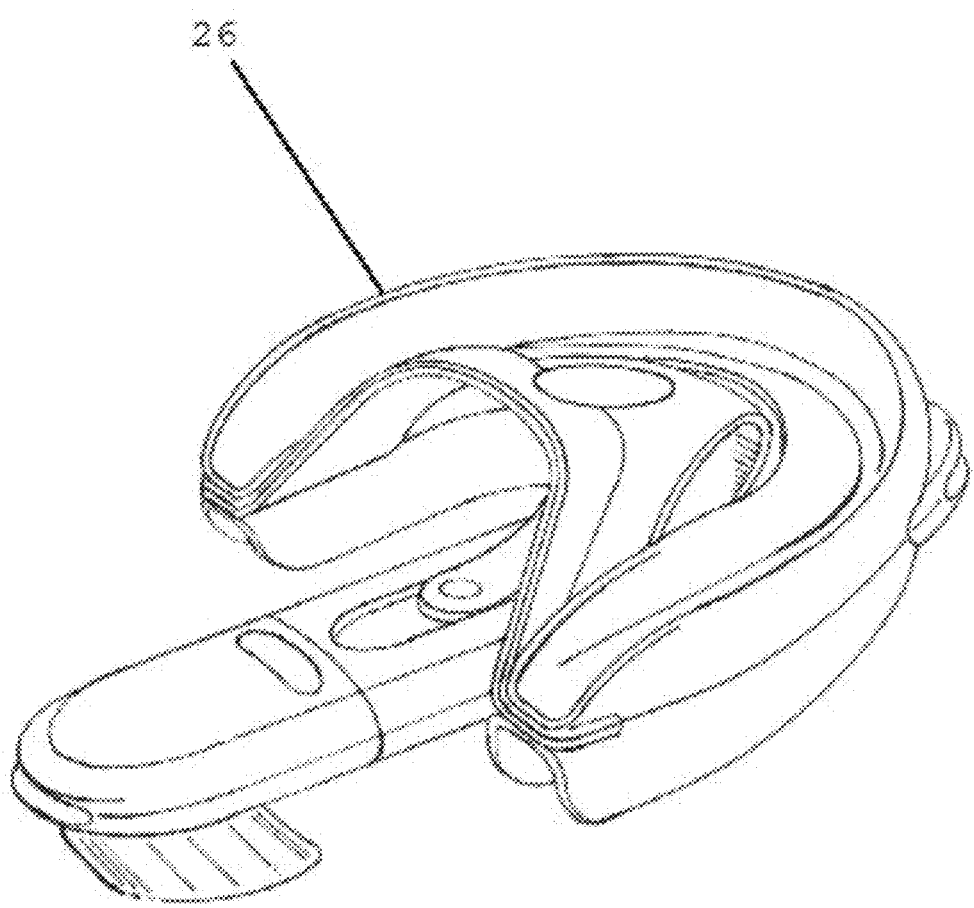
FIG. 3 is a rear perspective view of an integrated oral appliance 26.

FIG. 3 is a rear perspective view of an integrated oral appliance 26.

Figure 4:
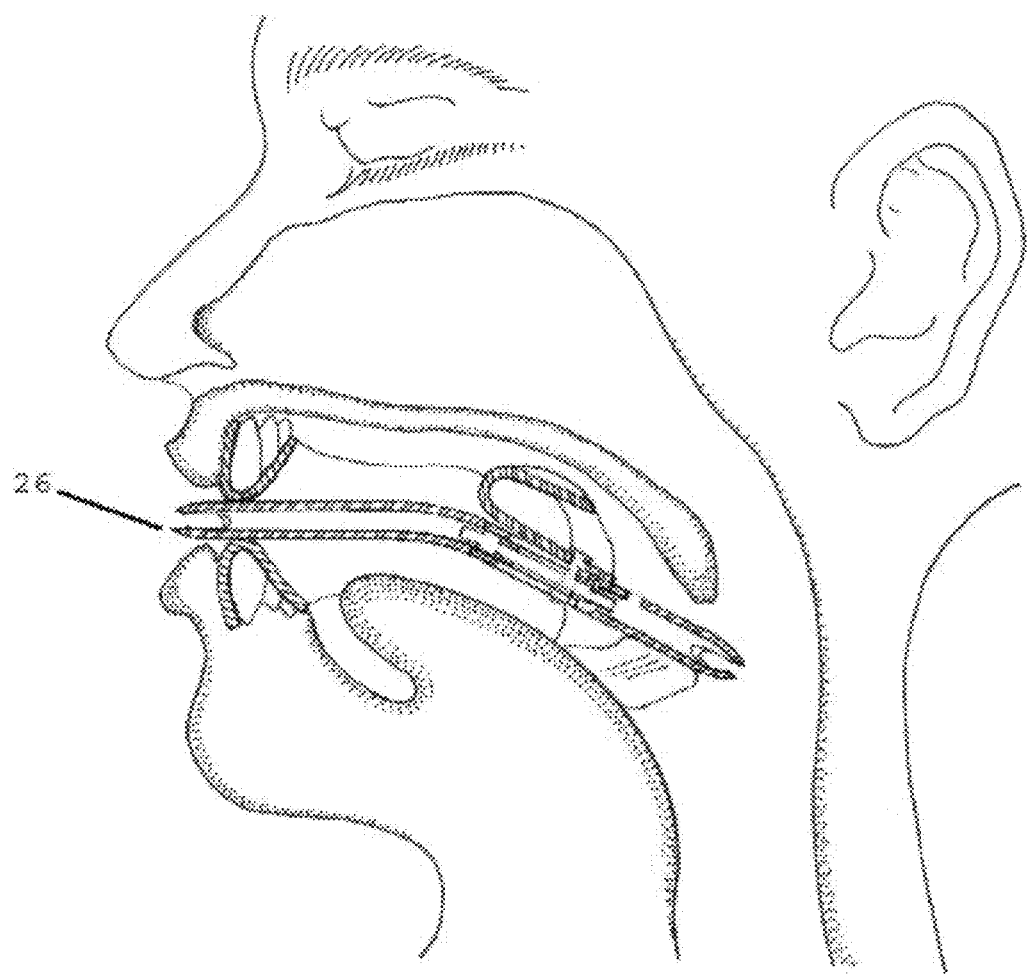
FIG. 4 is a left sectional view of an anatomical cross-section of a human upper airway (similar to FIG. 1), illustrating a cross-section of 26 positioned in the oral cavity, firmly gripping the upper and lower dentition, and interacting with the tongue to prevent it from obstructing the airway.

FIG. 4 is a left sectional view of an anatomical cross-section of a human upper airway (similar to FIG. 1) illustrating a cross-section of integrated oral appliance 26 positioned in the oral cavity, firmly gripping the upper and lower dentition, and interacting with the tongue to prevent it from obstructing the airway.

Figure 5:
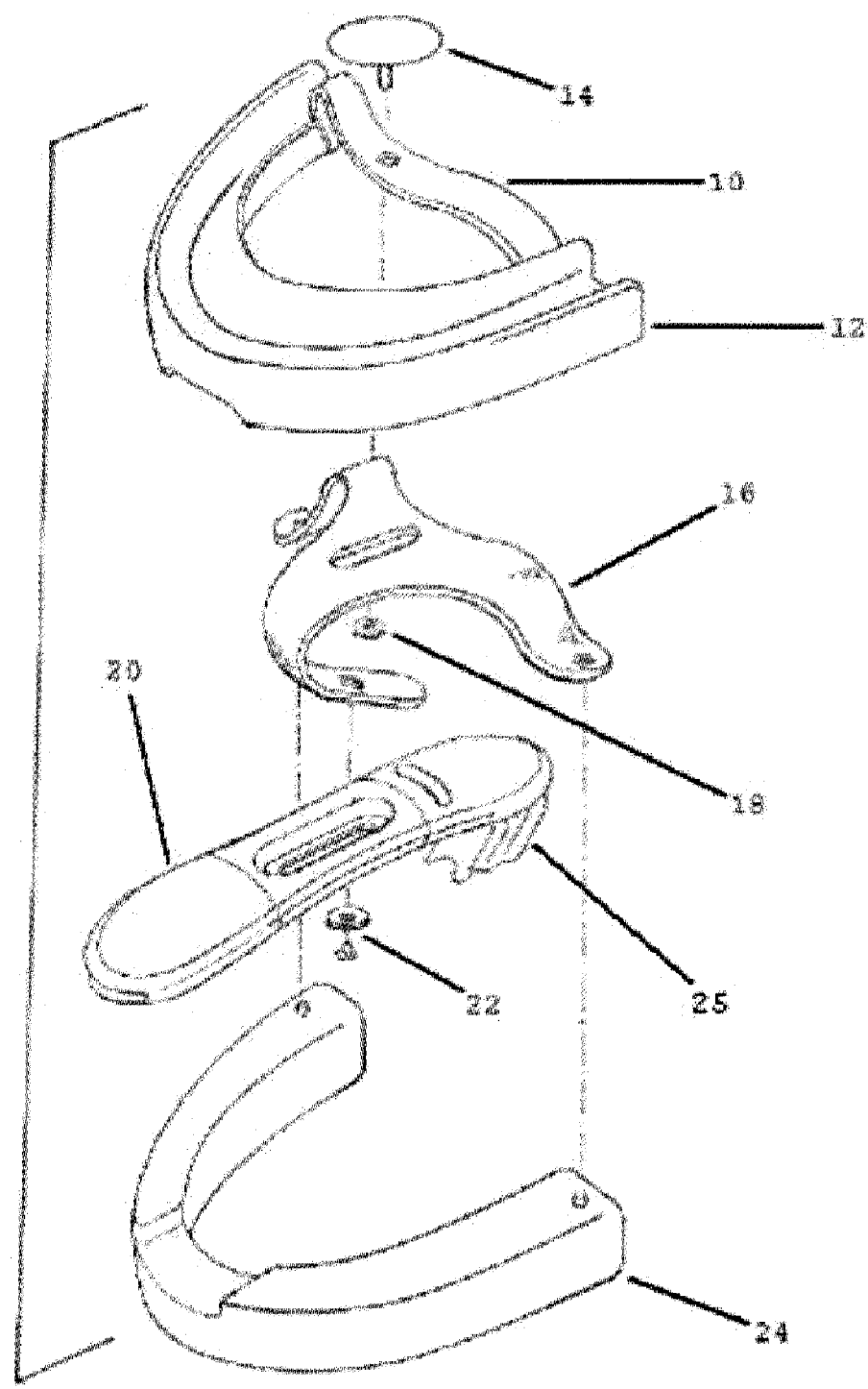
FIG. 5 is a front exploded perspective view of an integrated oral appliance 26 illustrating all elements.

FIG. 5 is a front exploded perspective view of (integrated oral appliance 26) illustrating all elements.

Figure 6:
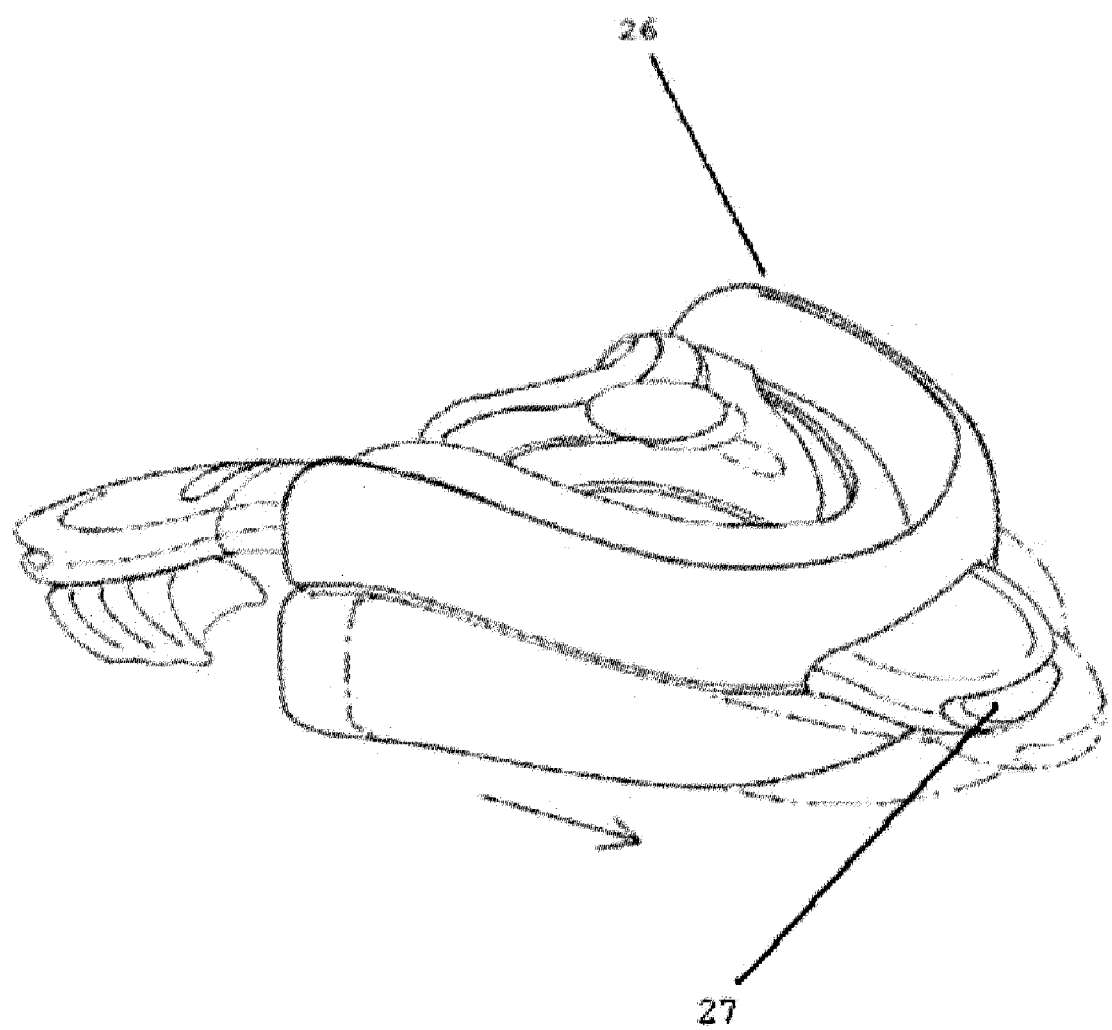
FIG. 6 is a left front perspective view of an integrated oral appliance 26 with an arrow illustrating advancement (repositioning) of the lower-tray 24 in an anterior direction.

FIG. 6 is a left front perspective view of integrated oral appliance 26 with an arrow illustrating advancement (repositioning) of lower-tray 24 in an anterior direction.

Figure 7:
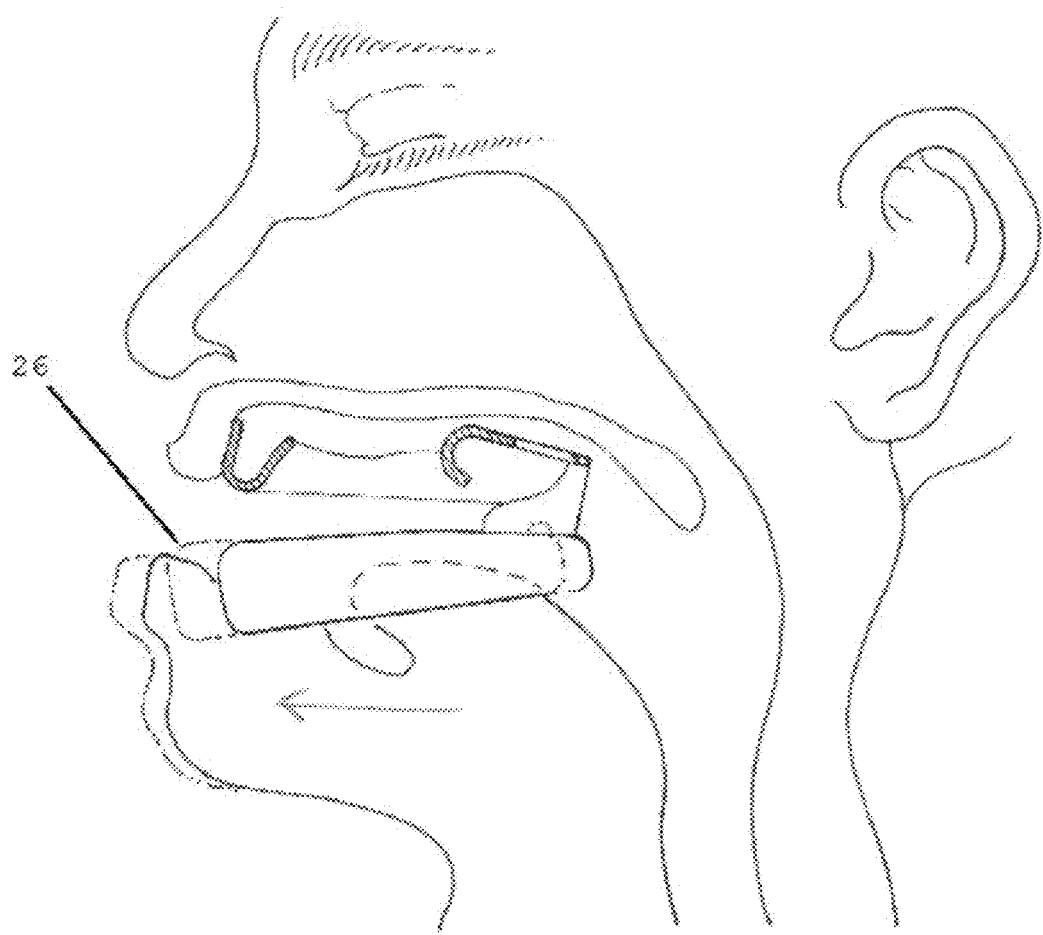
FIG. 7 is a left sectional view of an anatomical cross-section (similar to FIG. 4) illustrating anterior advancement of lower tray 24 to reposition the mandible from a neutral position, to further open the airway, and prevent occlusion within the pharynx.

FIG. 7 is a left sectional view (similar to FIG. 4) illustrating anterior advancement of lower-tray 24 to reposition the mandible from a neutral position, to further open the airway, and to prevent occlusion within the pharynx.

Figure 8:
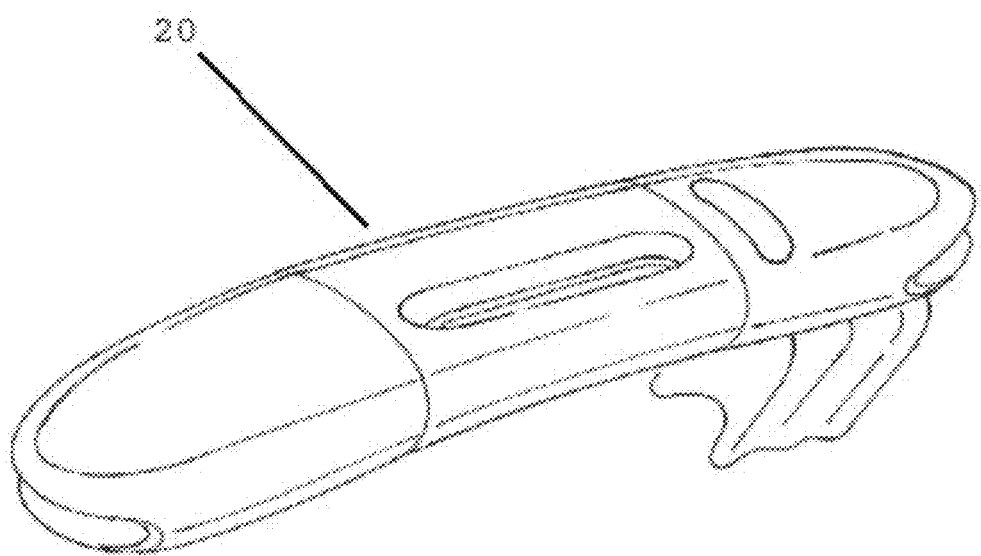
FIG. 8 is a top front perspective view of a tongue-restraint-ac 20.

FIG. 8 is a top front perspective view of the tongue-restraint-ac 20.

Figure 9:
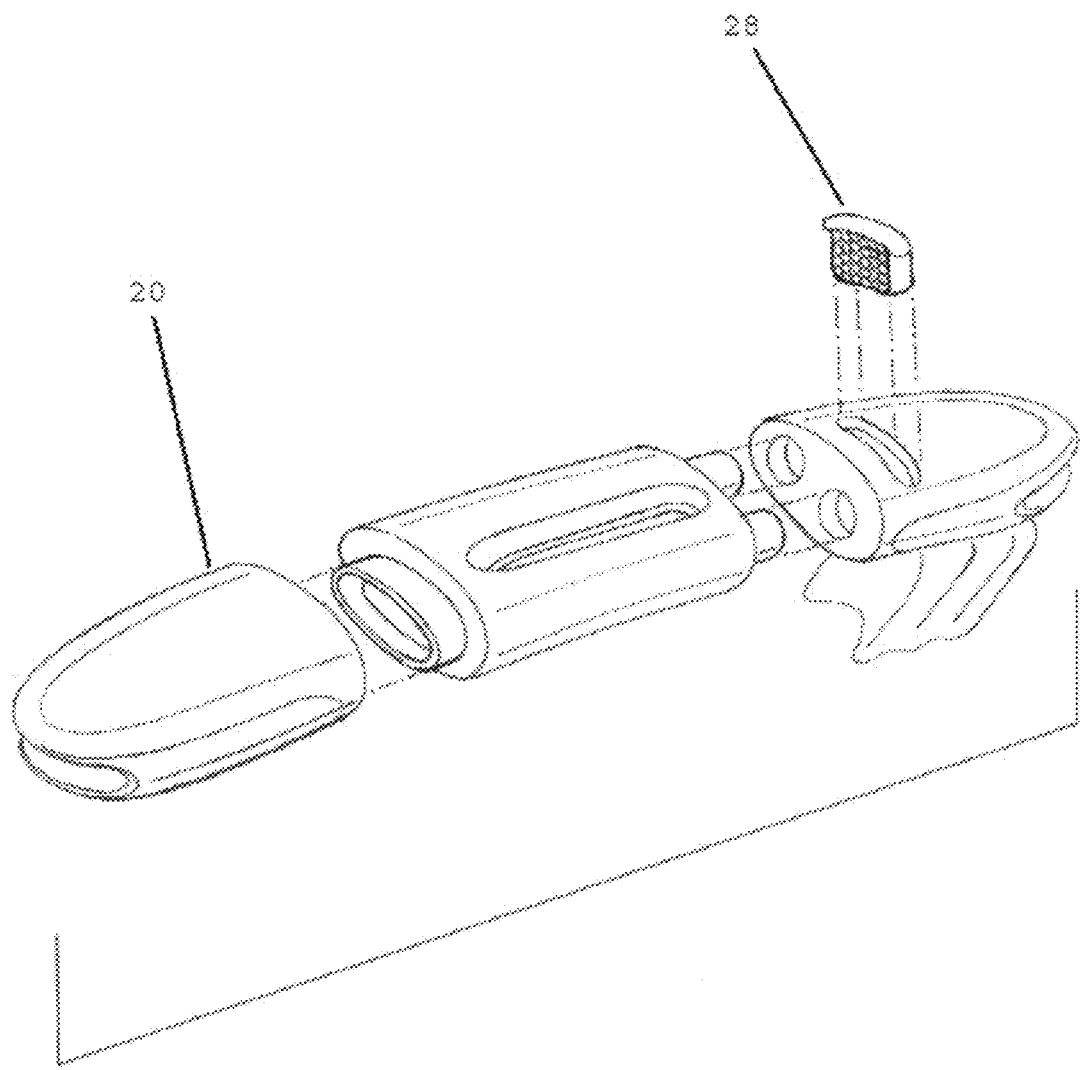
FIG. 9 is a front exploded perspective view of a tongue-restraint-ac 20 with heat-moisture-filter 28 removed.

FIG. 9 is a front exploded perspective view of tongue-restraint-ac 20 with heat-moisture-filter 28 removed.

Figure 10:
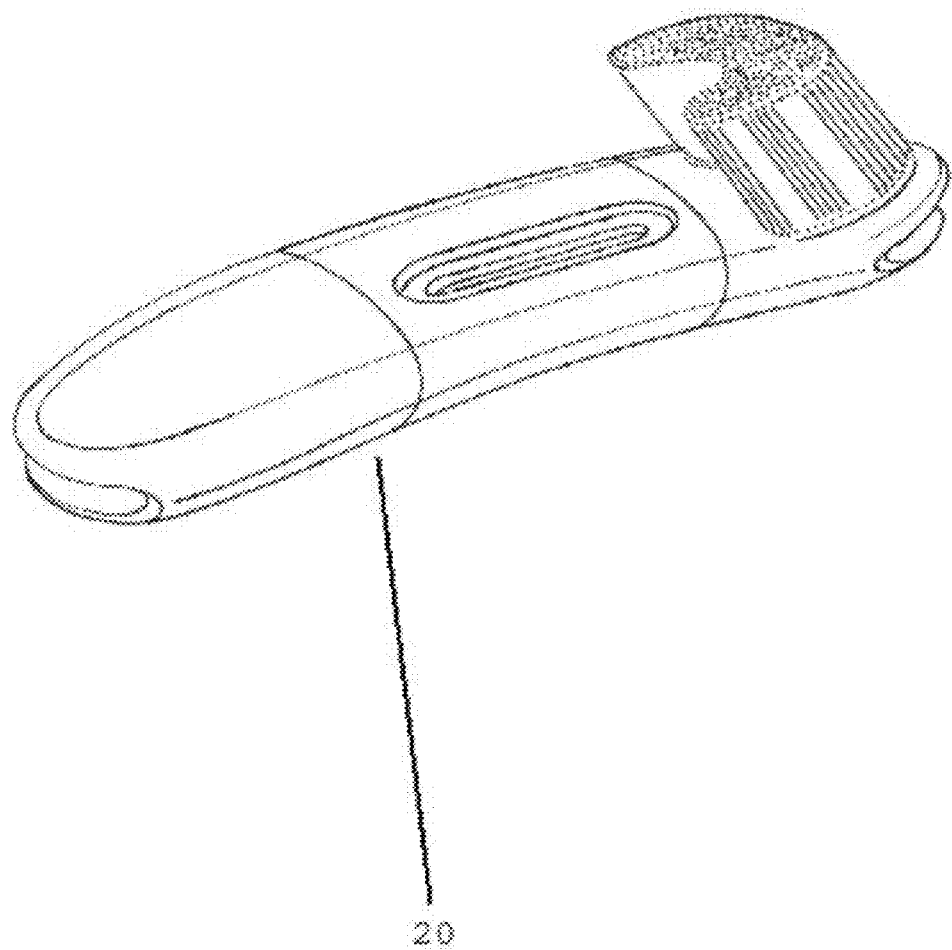
FIG. 10 is a front bottom perspective view of a tongue-restraint-ac 20.

FIG. 10 is a front bottom perspective view of a tongue-restraint-ac 20.

In operation, an appropriate medical professional (e.g. physician, dentist, etc.) initially adjusts integrated oral appliance 26 after the u-shaped upper-tray 12 and the u-shaped lower-tray 24 have been custom molded and fitted to conform to the users' dentition. Initial adjustment includes mandible repositioning and tongue-restraint-ac 20 adjusted to fit the users' tongue. In daily practice, prior to falling asleep, the user positions the integrated oral appliance 26 inside their oral cavity so that the u-shaped upper-tray 12 and lower-tray 24 firmly grips both upper and lower dentition. Both u-shaped trays are made from a biocompatible resilient material (e.g. thermoplastic such as ethylene vinyl acetate, or medical-grade silicone rubber, etc.) of a definite thickness to be strong enough to firmly grip the users' dentition, and firm enough to contain a built-in guide-bracket 10. Both u-shaped tray's also have sides to contain the flow of air to the center of both tray's. This prevents air from entering the oral cavity from the sides of both trays and restricts the air to flow through the open channel within the tongue-restraint-ac 20. In alternate embodiments other attachment means to the upper or lower dentition can comprise orthodontic materials including stainless steel, nickel titanium, polymers, or attachment means outside the oral cavity. In another embodiment the lower-tray 24 can also be fixed relative to the upper-tray 12.

The upper-tray 12 contains a guide-bracket 10 built into the back of the tray and attached to the inner surfaces of the left and right sides of the tray so as to form a bridge between the sides. The guide-bracket 10 supports and guides the flex-bracket 16 along an anterior-posterior path.

The guide-bracket 10 is made from a material that is biocompatible, rigid, and shaped to fit comfortably inside the oral cavity. The material can be polymeric, stainless steel, or any appropriate material that will functionally perform and will not rust or degrade when exposed to the environment inside the oral cavity. The guide-bracket 10 contains an opening in the middle to allow fastener-g 14 to connect the guide-bracket 10 to the flex-bracket 16 and fastener-fb 18.

The flex-bracket 16 is permanently attached to the rear of lower-tray 24, or in an alternate embodiment it can be removably attached. During initial setup, a medical professional adjusts lower-tray 24 (guided by the flex-bracket 16) in an anterior direction, to a position that is sufficient to prevent airway collapse without causing adverse effects. The flex-bracket 16 serves three functions. One function is to enable the attached lower-tray 24 to move the mandible to increase airway size. A second function is to provide a surface capable of generating a spring-loaded, compressive force when flexed. This surface also serves as the point of attachment (third function) for the tongue-restraint-ac 20. The tongue-restraint-ac 20 is attached to the flex-bracket 16 in a cantilevered fashion at its mid-section that contains a slot for adjustment. The tongue-restraint-ac 20 contains flexible bristles 25 built into (e.g. molded, implanted) its bottom rear surface to engage the dorsal surface of the tongue. The bristles maintain contact with the tongue under a compressive force that is sufficient to keep the bristles 25 engaged with the tongue to properly restrain it, but not excessive to cause pain or injury. The bristles 25 can be made from a polymeric material or another biocompatible appropriate material. In an alternate embodiment the bristles 25 can also be made using hollow fibers to allow time-released treatment solutions to flow into the dorsal surface of the tongue to treat other medical or nutritional conditions. In an alternate embodiment other materials can be used to engage the tongue.

The flex-bracket 16 is made from a material that is biocompatible, lightweight, strong enough to perform said function, and able to endure multiple flexures over the lifetime of integrated oral appliance 26. The material can be polymeric, stainless steel or any appropriate material(s) that will not rust or degrade when exposed to the environment inside the oral cavity. The spring-force range exerted by the flex-bracket 16 can be fixed or adjustable in an alternate embodiment. In alternate embodiments, the present invention can comprise a variety of spring types to exert the required force including leaf springs, torsion springs, etc.

The flex-bracket 16 contains an appropriately sized opening (e.g. slot) in the middle of the top surface to allow anterior-posterior adjustment and allow fastener-g 14 and fastener-fb 18 to connect the guide-bracket 10 to the flex-bracket 16. The flex-bracket 16 is appropriately shaped to enable it to be moved within the guide-bracket 10 in order to move the mandible.

The tongue-restraint-ac 20 comprises front, middle, and rear sections that are inter-connected to form an internal open air conduit 27 to allow passage of breathable air to bypass potential nasal restrictions and or airway obstructions. The air conduit 27 extends from the front section of the tongue-restraint-ac 20 to the rear section so that in one embodiment it will be positioned between the lips of the user and a location near the soft palate in the oral cavity. For example, in the event of nasal restriction, the user telescopically advances the front section to position it slightly beyond the front of the u-shaped trays so that the user's lips can surround it. Airflow within the air conduit 27 occurs naturally as the user inhales and exhales. When the user inhales, a negative pressure is developed within the pharynx (near the rear of the tongue-restraint-ac 20), causing air to flow from higher pressure (atmospheric pressure) outside the user's oral cavity directly to the user's pharynx. Airflow is reversed when the user exhales. Since the mouth is held closed via the u-shaped tray attachments to the upper and lower dentition, no untoward effects due to the oral cavity airflow should occur. If oral airflow is not required, the front of the tongue-restraint-ac 20 remains in the retracted position within the dimensions of the front of the u-shaped trays that are covered by the user's lips during sleep. In alternate embodiments the air conduit 27 can be made in different forms and shapes including round tubes, or, or in another embodiment the air conduit 27 can be eliminated if not required, or in another embodiment air can also flow via other channels.

The rear section of the tongue-restraint-ac 20 also has an opening in its top surface to allow a heat-moisture-filter 28 to be inserted into the air conduit 27 to provide heat and moisture to inspired air. The heat-moisture-filter 28 is also made to be changed on a daily basis. The heat-moisture-filter 28 can also be replaced by a solid filter to block airflow. In an alternate embodiment, the tongue-restraint-ac 20 can be provided without the heat-moisture-filter 28.

The middle section of the tongue-restraint-ac 20 is made of a rigid material (e.g. polymer) and includes a slot in the middle (referred to above) that is open at the top and bottom. An appropriate fastener-trac 22 is used to connect the tongue-restraint-ac 20 to the flex-bracket 16. The slot enables the tongue-restraint-ac 20 to be adjusted for proper positioning on the dorsal surface of the tongue.

The heat-moisture-filter 28 contains an outer shell made from a rigid material (e.g. biocompatible polymer) and an inner corrugated paper rolled to fit within the outer shell. The paper is made of a material suitable to absorb heat and moisture from expired air and release heat and moisture into inspired air. The paper can be made from a cellulose material or another appropriate material with heat/moisture characteristics. Also, in an alternate embodiment, if the user does not want air to flow through the tongue-restraint-ac 20 then a solid material can be substituted for the corrugated material to prevent airflow. In another alternative embodiment, a treatment can also be added to the enclosed filter material to provide for other medical or nutritional needs, etc.

The front section of the tongue-restraint-ac 20 provides an entrance to allow air to enter and leave the tongue-restraint-ac 20 during inspiration and expiration. This section is made using a sufficiently flexible material to allow the tongue-restraint-ac 20 to flex within the confines of the upper-tray 12 and lower-tray 24 in concert with superior-inferior tongue movement.

Thus, it can be seen from the above illustrative embodiments that key elements of the integrated oral appliance 26 interact with upper airway tissue to treat upper airway abnormalities that cause obstructions during sleep. When positioned in a user's mouth (oral cavity), the integrated oral appliance 26 restrains the tongue, preventing the tongue from moving into airway space; moves the mandible in an anterior (forward) direction to open the airway; and reduces tissue pressure to improve airflow. The present invention also provides an air conduit 27 that's built into the tongue-restraint-ac 20 to bypass nasal restrictions and or airway obstructions if they occur. To prevent inspired air from cooling and drying the pharynx, the tongue-restraint-ac 20 contains a heat-moisture-filter 28 that captures the heat and moisture from the expired air and releases heat and moisture to the drier inspired air. After use, the user removes the integrated oral appliance 26 from the oral cavity. Appropriate means are also used to clean the integrated oral appliance 26.

In an actual reduction to practice the present invention, involving a moderate OSA condition, eliminated snoring and airway obstructions and raised oxygen saturation from 87% (without the integrated oral appliance 26) to 100% using the integrated oral appliance 26.

Additional Embodiments

It should be obvious to those skilled in the art that there are a wide variety of changes that can be made to either the integrated oral appliance 26 or it's method of manufacture. In one alternate embodiment, the present invention can be made with only one of the key features such as with tongue restraint only or with mandible advance only. In another embodiment tongue restraint can be accomplished with attachment to upper dentition or lower dentition using either the upper-tray 12 alone or the lower-tray 24 alone. Tongue restraint can also be accomplished without an internal air conduit 27 if an alternate breathing passage is not required. In other embodiments there can be variations in adjustable features such as adjustable spring force or the type of spring used. In another embodiment the bristle element 25 can be replaceable to accommodate wear or made out of a different material that also has non-slip properties. In other embodiments there can be variations in the method of mandible adjustment.

Particular embodiments of the present invention have been presented for purposes of illustration and description, and are not intended to be exhaustive or limited to the invention in the form disclosed. Many modifications and variations will be apparent to those skilled in the art. The preferred embodiment was chosen and described in order to best explain the principles of the invention, the basic and practical application, and to enable others of ordinary skill in the art to understand the invention with various embodiments and various modifications as are suited to the particular use contemplated.

Having thus described the invention, what is desired to be protected by Letters Patent is presented in the subsequently appended claims.

What is claimed is:

1. An oral appliance comprising a tray shaped to engage at least a portion of dentition and a tongue restraint coupled as a cantilever through a spring-force applying attachment to a rigid bracket coupled to the tray; wherein the spring-force attachment is a flexible bracket adjustably coupled to the rigid bracket for anterior and posterior adjustment of the flexible bracket and tongue restraint along forward and rearward positions within a mouth.

2. The oral appliance of claim 1, wherein the tongue restraint includes one or more projections.

3. The oral appliance of claim 2, wherein the one or more projections include bristles.

4. The oral appliance of claim 3, wherein one or more bristles are hollow and contain at least one treatment of a medical treatment and nutritional treatment.

5. The oral appliance of claim 4, wherein the at least one treatment is a time-release treatment.

6. The oral appliance of claim 2, wherein the spring-force applying attachment applies adjustable force.

7. The oral appliance of claim 2, wherein the tongue restraint includes an end including the one or more projections that is distance-adjustable relative to a front of the tray.

8. The oral appliance of claim 2, wherein the rigid bracket is coupled to points on opposing halves of the tray.

9. The oral appliance of claim 1, further comprising an air conduit.

10. The oral appliance of claim 9, further comprising a filter material in the air conduit.

11. The oral appliance of claim 10, wherein the filter material includes at least one of a medicine and nutrient.

12. The oral appliance of claim 10, wherein the filter material absorbs heat and moisture from expired air and releases heat and moisture into inspired air.

13. The oral appliance of claim 10, wherein the filter material is removable and replaceable.

14. The oral appliance of claim 1, further comprising an air conduit in the tongue restraint traversing both an outermost and innermost wall of the tray wherein the conduit includes a front air opening in an end of the tongue restraint positioned forward of the tray.

15. The oral appliance of claim 14, further comprising a filter material in the air conduit.

16. The oral appliance of claim 15, wherein the filter material is removable and replaceable.

17. The oral appliance of claim 15, wherein the filter material includes at least one of a medicine and nutrient.

18. The oral appliance of claim 15, wherein the filter material absorbs heat and moisture from expired air and releases heat and moisture into inspired air.

19. The oral appliance of claim 1, wherein said tray is one of a lower and upper tray coupled to each other, and wherein each tray is shaped to engage a dentition.

20. The oral appliance of claim 19, wherein a front of the lower tray is forward adjustable relative to a front of the upper tray.

21. The oral appliance of claim 20, further comprising an air conduit with a front air opening in an end of the air conduit positioned forward of the trays.

22. The oral appliance of claim 1, wherein the tongue restraint comprises a non-slip material.

23. The oral appliance of claim 22, further comprising an air conduit traversing both an outermost and innermost wall of the tray wherein the conduit includes a front air opening in an end of the air conduit positioned forward of the tray.

24. The oral appliance of claim 23, wherein the air conduit is within the tongue restraint.

25. The oral appliance of claim 1, wherein the tongue restraint includes an end with material for contacting the tongue that is distance-adjustable relative to a front of the tray.

26. The oral appliance of claim 1, wherein the spring-force applying attachment applies adjustable force.

27. The oral appliance of claim 1, wherein the rigid bracket is coupled to points on opposing halves of the tray.

* * * * *